(12) United States Patent
Gielen (10) Patent No.: US 7,295,880 B2
(45) Date of Patent: Nov. 13, 2007

(54) STIMULATION CONTROL FOR BRAIN STIMULATION

(75) Inventor: Frans L. H. Gielen, Eckelrade (NL)

(73) Assignee: Medtronic, Inc., Minneapolis, MN (US)

( * ) Notice: Subject to any disclaimer, the term of this patent is extended or adjusted under 35 U.S.C. 154(b) by 768 days.

(21) Appl. No.: 10/133,466

(22) Filed: Apr. 29, 2002

(65) Prior Publication Data

US 2003/0204219 A1    Oct. 30, 2003

(51) Int. Cl.
*A61N 1/00* (2006.01)
(52) U.S. Cl. ........................................ 607/72
(58) Field of Classification Search ................. 607/45, 607/46, 72–74, 1, 2, 62–64; 128/898
See application file for complete search history.

(56) References Cited

U.S. PATENT DOCUMENTS

| | | | |
|---|---|---|---|
| 4,232,679 A | 11/1980 | Schulman | |
| 4,290,429 A | 9/1981 | Blaser | |
| 4,390,020 A | 6/1983 | Herpers | |
| 4,952,864 A | 8/1990 | Pless et al. | |
| 5,179,950 A | 1/1993 | Stanislaw | |
| 5,344,431 A | 9/1994 | Merritt et al. | |
| 5,354,320 A | 10/1994 | Schaldach et al. | |
| 5,733,313 A | 3/1998 | Barreras, Sr. et al. | |
| 5,735,887 A | 4/1998 | Barreras, Sr. et al. | |
| 5,807,397 A | 9/1998 | Barreras | |
| 5,869,970 A | 2/1999 | Palm et al. | |
| 5,876,425 A | 3/1999 | Gord et al. | |
| 5,941,906 A | 8/1999 | Barreras, Sr. et al. | |
| 5,991,664 A | 11/1999 | Seligman | |
| 5,991,665 A | 11/1999 | Wang et al. | |
| 6,154,675 A | 11/2000 | Juran et al. | |
| 6,227,203 B1 * | 5/2001 | Rise et al. | 128/898 |
| 6,317,634 B1 | 11/2001 | Lyden | |
| 6,484,059 B2 * | 11/2002 | Gielen | 607/45 |
| 6,704,603 B1 * | 3/2004 | Gesotti | 607/62 |
| 2002/0161403 A1 * | 10/2002 | Meadows et al. | 607/1 |
| 2003/0074037 A1 * | 4/2003 | Moore et al. | 607/63 |

FOREIGN PATENT DOCUMENTS

| | | |
|---|---|---|
| JP | 640662 | 3/1994 |
| JP | 965635 | 3/1997 |
| WO | WO 99/06108 | 2/1999 |

OTHER PUBLICATIONS

Implantable Neurostimulation Systems Brochure, 1998, Medtronic, Inc.

* cited by examiner

*Primary Examiner*—George Manuel
(74) *Attorney, Agent, or Firm*—John W. Albrecht (57) ABSTRACT

System and method for end of battery life operation of an implantable bilateral brain stimulator. The present system and method automatically measures one or more levels of electrical parameters in a battery system of the implantable stimulator. The measurement can be compared to threshold values. The implantable bilateral brain stimulator can then make automatic adjustments to the therapy when the levels of the electrical parameters in the battery system reach the threshold values. Adjustments to the therapy are made such that the patient is provided with an adjusted, but sufficiently safe, amount of therapy so as to extend the life of the battery and also to allow some physical symptoms alleviated by the system to return, thereby signaling the patient that medical attention needs to be sought.

33 Claims, 4 Drawing Sheets

STIMULATION CONTROL FOR BRAIN STIMULATION

TECHNICAL FIELD

The invention relates to bilateral stimulation of the brain and, more particularly, to control of bilateral stimulation of the brain.

BACKGROUND

Parkinson's disease (PD) is a degenerative disorder of the nervous system. PD results from the progressive death of a specific group of nerve cells in a layer of a region of the substantia nigra in the midbrain. These nerve cells, or neurons, produce a chemical messenger or neurotransmitter called dopamine that enables them to communicate with receptors on neurons in another region of the brain called the basal ganglia. As these nerve cells die, there is a depletion of dopamine in the basal ganglia. In addition to the depletion of dopamine, there is also an over-excitement of the glutamateric NMDA receptors in the subthalamic nucleus (STN). This occurs in a pathophysiological circuit that results in bradykinesia, muscle rigidity, and tremors in the patient.

As there are no cures for PD. A patient's only option is to treat the symptoms of their PD. The major objective in treating PD is to improve the quality of the patient's life. This is done through treating the patient's symptoms so as to maintain the functional status of the patient. Treating PD can include the use of drugs and/or implantable pulse generator systems. Drugs for treating PD target the neurochemistry of specific neurotransmitters, such as acetylcholine, dopamine, and seotonin. Some drugs cause a reduction in the amount acetylcholine in the basal ganglia to offset the lack of dopamine from the substantia nigra. Other drugs add more dopamine, cause more dopamine to be produced, and/or block the reuptake of dopamine in the brain so as to replenish the amount of dopamine not being supplied. Additional drugs exist that mimic the action of dopamine or slow the breakdown of dopamine.

Deep brain stimulation (DBS) is also used in treating patients with PD. In DBS, a multi-electrode lead is implanted into specific areas of the brain. These areas include the ventrointermediate nucleus of the thalamus. The lead is coupled to a pulse generator that is implanted under the skin of the patient. The patient uses a hand-held magnet to turn the pulse generator on or off. The pulse generator produces high-frequency electrical pulses that are delivered to the thalamus by the implanted electrodes. Electrically stimulating the thalamus blocks many of the symptoms of PD.

Bilateral DBS is also possible. In bilateral DBS, two multi-electrode leads are implanted into the brain of the patient. Each lead is implanted in the same general brain structure on each half of the brain. So, for bilateral stimulation of the subthalamic nucleus or pars interna of the globus pallidus, there is one multi-electrode lead implanted into each half of the structure that is present in each half of the brain. Bilateral stimulation in these regions of the brain has been associated with major improvements in motor function in patients with PD.

The pulse generator must be replaced when the batteries of the device no longer supply adequate power to the pulse generator. The time until the pulse generator needs to be replaced is dependent, in part, on the operation time and pulse characteristics of the pulse generator. Allowing the battery to deplete itself to a level that the pulse generator can no longer provide adequate therapy, or stops working altogether, can be problematic for the patient. Therefore, there is a need for providing continued PD therapy as the battery of an implantable pulse generator's nears the end of its life.

Power management and conservation in pulse generators has been recognized. Table 1, and others listed herein, lists documents that suggest power conservation and management schemes for pulse generators.

TABLE 1

| Patent Number | Inventors | Title |
| --- | --- | --- |
| 6,317,634 | Lyden | Implantable Cardiac Stimulating Device with Optimized Demand |
| 5,869,970 | Palm et al. | Power Management System for an Implantable Device |
| 4,952,864 | Pless et al. | Power Supply Down-Conversion, Regulation and Low Battery Detection System |
| 4,390,020 | Herpers | Implantable Medical Device and Power Source Depletion Control Therefor |
| 4,290,429 | Blaser | Battery Monitoring Circuit in a Cardiac Pacemaker |

All documents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention. In addition, providing the documents listed in Table 1, or elsewhere in this document, is not an admission that the cited document is prior art to the present invention.

SUMMARY

The present invention has certain objects. That is, various embodiments of the present invention provide solutions to one or more problems existing in the prior art with respect to the operation of implantable bilateral brain stimulators, and with respect to end of battery life operation for implantable bilateral brain stimulators in particular. Such problems include, for example, the sudden loss of therapy from a bilateral brain stimulator due to the battery end of life. In this situation, the patient can be left without therapy from the implantable stimulator. Various embodiments of the present invention have the object of solving the foregoing problem.

In comparison to known implementations of providing end of battery life operation for an implantable medical device, various embodiments of the present invention may provide one or more of the following advantages: adjusting the therapy provided by the implantable medical device when the level of electrical energy in the battery reaches a preselected threshold; adjusting the therapy provided by the implantable bilateral brain stimulator in such a way that the patient is provided with an adjusted, but sufficiently safe, amount of therapy; adjusting the amount of therapy provided by the implantable bilateral brain stimulator to extend the life of the battery; adjusting the amount of therapy provided by the implantable bilateral brain stimulator to allow some physical symptoms alleviated by the system to return, thereby signaling the patient that medical attention needs to be sought.

Objects of the present invention overcome at least some of the disadvantages of the foregoing systems by providing a system and method that measures a level of electrical energy parameter in the battery system of the implantable system and adjusts the therapy provided by the implantable system when the level of the electrical energy reaches the preselected threshold. In one example, the present invention provides a system and method of automatically measuring the level of electrical energy in the battery of the implantable system and comparing the level to one or more preselected thresholds. In an additional example, the present invention provides an implantable system and method of automatically adjusting therapy provided by the implantable system when the level of electrical energy reaches one or more of the preselected thresholds.

In addition, the invention provides an implantable brain electrical system and method for automatically measuring the level of electrical energy in the battery of the implantable brain electrical system and comparing the level to one or more preselected thresholds. In an additional example, the present invention provides an implantable brain electrical system and method of automatically adjusting therapy provided by the implantable system when the level of electrical energy reaches one or more of the preselected thresholds. Furthermore, the invention provides a brain electrical stimulation system and method for extending the life of the power source of the brain electrical stimulation system. Also, the invention provides a brain electrical stimulation system and method for adjusting the amount of therapy provided by the implantable bilateral brain stimulator to allow some physical symptoms alleviated by the system to return, thereby signaling the patient that medical attention needs to be sought.

Various embodiments of the invention may possess one or more features capable of fulfilling the above objects. Instead of relying upon a patient to monitor the energy level of a battery in their implantable medical device, the present invention provides an implantable system and method for automatically measuring the level of electrical energy of the electrical energy supply and adjusting the electrical energy pulses from the stimulation unit when the level of the electrical energy parameter reaches the preselected threshold.

The system and method of the present invention can also be customized for each patient's power use requirements. For example, based on the demand placed on the electrical power supply by the patient's brain stimulation regimen, the preselected threshold can be programmed by a physician to allow sufficient time once the threshold is reached for the patient to present themselves to the physician for replacement of the implantable stimulation unit. In addition, the nature of the physical symptoms that return once the threshold is reached can also be customized and experienced during the implanting of the brain electrical stimulation system. Having had experienced these customized symptoms, the patient will more easily recognize the situation with the stimulation system when these symptoms return in the future.

Some embodiments of the invention include one or more of the following features: a first brain stimulation lead that includes an electrode; a second brain stimulation lead that includes an electrode; an implantable brain stimulation pulse generator unit having the electrode of the first brain stimulation lead and the electrode of the second brain stimulation lead operatively coupled thereto; an electrical power supply in the implantable brain stimulation pulse generator unit; a signal analyzer coupled to the electrical power supply, where the signal analyzer is operable to provide electrical pulses to the electrode on the first brain stimulation lead and the electrode on the second brain stimulation lead; and a power monitor operatively coupled to the stimulation unit, where the power monitor is operable to measure a level of an electrical energy parameter for the electrical power supply and is operable to cause the stimulation unit to adjust electrical pulses to the electrode on the first brain stimulation lead when the level of the electrical energy parameter reaches the preselected threshold.

The invention involves managing the electrical energy resources of an implantable brain stimulation system. Electrical pulses are provided to a first brain location and a second brain location using the battery. The level of an electrical energy parameter of the battery is measured and compared to the preselected threshold. The electrical pulses to at least the first brain location are then adjusted when the level of the electrical energy parameter reaches the preselected threshold.

In one embodiment, the present invention provides for electrical pulses to be continuously provided to the first brain location and the second location using the battery. The electrical pulses delivered to the first and second brain sites are defined by programmable parameter values, such as the frequency, amplitude, waveform, voltage and duration of the pulses. In addition to providing the electrical pulses, a monitoring interval is also counted down, where the monitoring interval is the time between measurements of the level of electrical parameter of the battery. When the monitoring interval, the level of at least one of the electrical energy parameters of the battery are measured. Any number of electrical energy parameters can be used in measuring the battery.

The level of the electrical energy parameter can then be compared to the preselected threshold. A determination is then made as to whether the level of the electrical energy parameter has, or has not, exceeded the preselected threshold. When the electrical energy parameter fails to exceed the preselected threshold, the system continues to provide electrical energy to the first and second brain locations. In addition, the system also starts a new monitoring interval. Alternatively, when the electrical energy parameter exceeds the preselected threshold, the electrical pulses to the first brain location are adjusted according to the present invention.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DESCRIPTION OF THE EMBODIMENTS

The present invention involves techniques for preventing a sudden loss of therapy from an implantable bilateral brain stimulator. The sudden loss of therapy can be due to a battery that is powering the implantable bilateral brain stimulator reaching its end of life. For example, when the battery reaches its end of life, the implantable system can stop providing therapy. As a result, the patient can be left without therapy from the implantable system. In contrast to leaving the patient without therapy from the implantable system once the battery reaches its end of life, the present invention allows for an adjustment in the amount of therapy that is delivered to the patient. The adjustment in the amount of therapy delivered to the patient serves not only to extend the life of the battery, but also serves to allow some physical symptoms alleviated by the system to return, thereby signaling the patient that medical attention needs to be sought.

The present invention allows for measuring a level of electrical energy in the battery of the implantable system. The level can then be compared to one or more preselected thresholds. The therapy provided by the implantable system can then be adjusted when the level of electrical energy in the battery reaches the preselected threshold. The present invention adjusts the therapy provided by the implantable bilateral brain stimulator in such a way that the patient is provided with, besides other things, an adjusted, but sufficiently safe, amount of therapy. Adjusting the therapy can increase the battery life due to less demand being placed on the battery, and can also serve to allow some physical symptoms alleviated by the system to return, thereby signaling the patient that medical attention needs to be sought.

The use of bilateral brain stimulation in the subthalamic nucleus or the globus pallidus with implantable brain stimulation systems has been very effective in treating neurological disorders. For example, bilateral subthalamic nucleus stimulation is highly effective in treating patients with Parkinson's disease. Bilateral brain stimulators provide more therapy options for the patient as compared to unilateral brain stimulators. As such, most patients in need of a brain stimulator receive a dual channel stimulator.

Currently, implantable bilateral brain stimulators include a single battery as the power source. In these systems, this single power source is responsible for powering one or more stimulation channels. For example, the single power source can power at least two stimulation channels. The battery of the bilateral brain stimulator, however, has a finite life. This means that at some point, the battery has the potential for failing to provide adequate power to the implantable system. If this were to happen, both channels of the bilateral brain stimulator could fail to operate, leading to an undesirable situation for the patient.

One example of an undesirable situation arising from the failure of a bilateral brain stimulator could occur in patients being treated for Parkinson's disease. Patients being treated for Parkinson's disease have received highly effective therapy with bilateral brain stimulators. Most of these patients are severely ill before receiving their bilateral brain stimulators, and most of them experienced severe disease symptoms when not being treated with medication. These severe disease symptoms can include akinesia and dystonia. Akinesia involves the loss of voluntary motion, and dystonia involves involuntary muscle contractions that force certain body parts into abnormal, sometimes painful, movements or postures. These conditions can affect any part of the body. Thus, ensuring that the effects of one or more of these conditions are minimized when the battery of the patient's bilateral brain stimulator begins fail can be important.

About thirty percent of the bilateral stimulation patients also need to reduce or eliminate any Parkinson's medication they may be taking. This percentage is likely to increase as therapy with the bilateral stimulators becomes more effective. This means that more and more Parkinson's patients will become completely dependent on the treatment provided by their bilateral brain stimulator. Patients who have been treated exclusively with bilateral brain stimulation for a significant length of time are also known to respond differently to subsequent anti-Parkinson's medications than before the bilateral brain stimulation. Some patients may, therefore, not experience sufficient treatment from anti-Parkinson's medication to prevent an akinetic crisis if the battery of their implantable bilateral brain stimulator were to fail.

From experience with unilateral brain stimulators, it is known that unilateral stimulation can partially suppress Parkinson's disease symptoms predominantly in one half of the body and partly in the head neck and trunk. The result is that laryngeal dystonia is unlikely to occur in patients with unilateral brain stimulators. As the Parkinson's disease symptoms are only partially suppressed along the midline of the body, some Parkinson's disease symptoms may remain when unilateral brain stimulation is being used. However, the most undesirable Parkinson's disease symptoms can be suppressed.

While many of the examples presented below are directed to the detection and treatment of Parkinson's disease, it is recognized that the present invention is not limited only to the treatment of Parkinson's disease. For example, the present invention can be used to treat any number of neurological conditions within the brain. Examples of these conditions include, but are not limited to, migraine headaches, schizophrenia, depression, mania, dystonia, or other neurological disorders where a sudden and complete loss of therapy from an implantable medical device would be undesirable to the patient.

Figure 1:
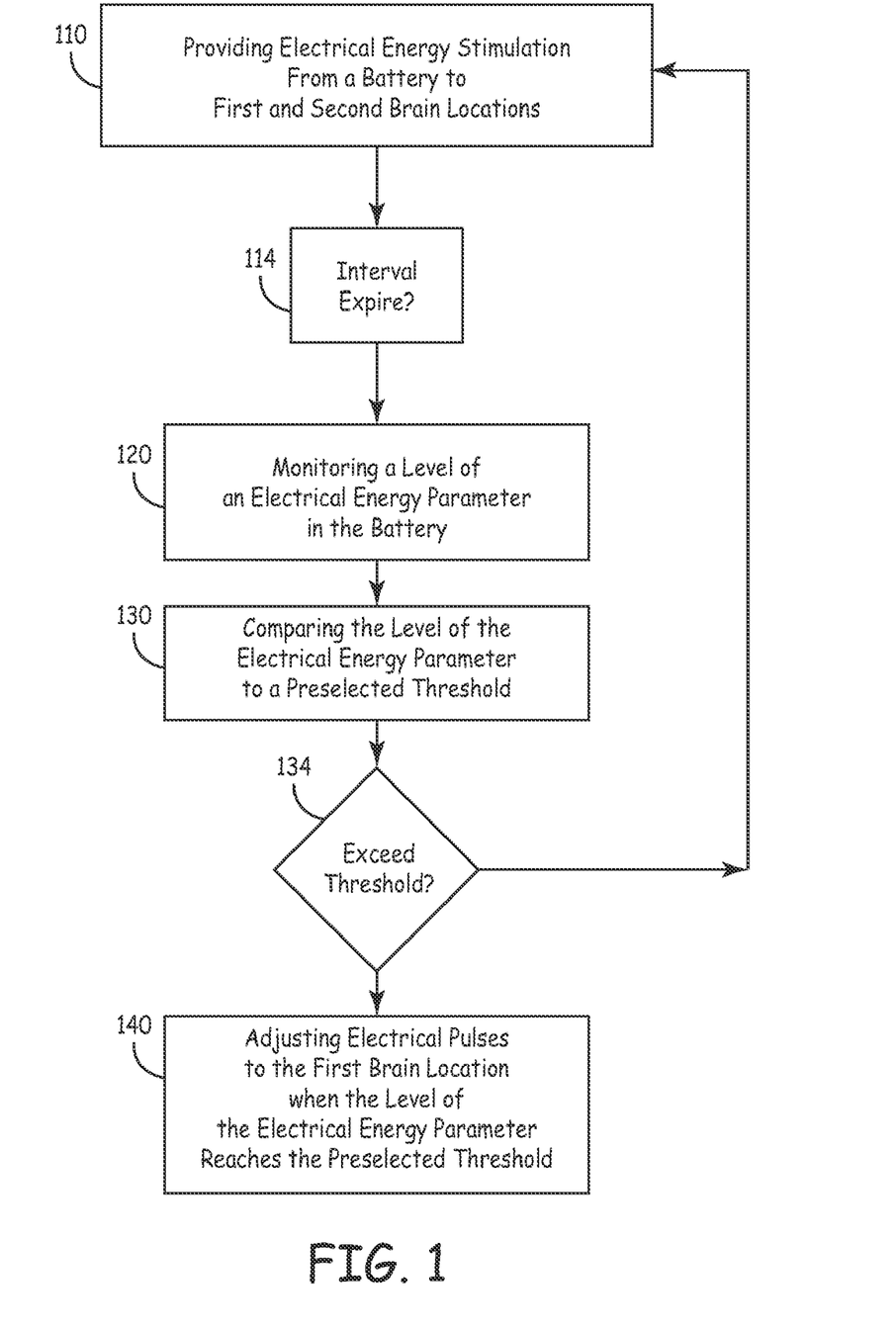
FIG. 1 is a flow chart illustrating a technique for adjusting electrical pulses to a first brain location according to one embodiment of the present invention.

FIG. 1 is a flow diagram illustrating a method of providing electrical energy stimulation to a brain of a patient according to one embodiment of the present invention. At 110, electrical energy stimulation in the form of electrical pulses using a battery is preferably continuously provided to a first brain location and a second brain location. For the present invention, the battery can take the form of most any depletable energy source. For example, the battery can be formed from one or more electrochemical cells suitable for use in an implantable medical device.

Electrical stimulation according to the present invention can take the form of deep-brain stimulation (DBS) of the first and second brain locations. In one embodiment, DBS of the first and second brain locations target bilateral segments of the subthalamic nucleus or the internal part of the globus pallidus. Alternatively, the first and second brain locations can be bilateral segments of other brain structures. It is also possible that the first brain location can be in a first brain structure of a right hemisphere of the brain, while the second brain location can be in a second brain structure of a left hemisphere of the brain.

In addition, the first and second brain locations can both be located in a single hemisphere of the brain (e.g., first and second brain locations in a left hemisphere of the brain, or first and second brain locations in a right hemisphere of the brain). In this latter example, the first and second brain locations can be in the same structure of the single hemisphere of the brain. Alternatively, the first and second brain locations can be in different structures of the single hemisphere of the brain.

In one example, the electrical energy pulses of the DBS to the first and second brain locations are delivered to bilateral portions of the brain. For example, the first brain location can include a first half of the subthalamic nucleus in a first hemisphere of the brain, while the second location can include a second half of the subthalamic nucleus in a second hemisphere of the brain. Alternatively, the first brain location can include a first half of the globus pallidus internae in the first hemisphere of the brain, while the second location can include a second half of the globus pallidus internae in the second hemisphere of the brain. Other first and second brain locations are also possible. The exact location for the electrical energy pulses will be dependent upon the patient and/or the condition being treated.

The electrical pulses delivered to the first and second brain sites are defined by programmable parameter values. Programmable parameters of the pulses used in the present invention include, but are not limited to, the frequency and the duration of the pulses, the waveform of the pulses, and the voltage for each of the electrical pulses. For example, each electrical pulse of the electrical pulses of the present invention can have a programmable pulse duration of at least thirty (30) microseconds. Alternatively, the pulse duration is at least sixty (60) microseconds. The pulse duration can also be at least four hundred fifty 450 microseconds. The programmable pulse duration can also be ten (10) milliseconds or less. Alternatively, the pulse duration can be four hundred fifty (450) microseconds or less. The pulse duration can be sixty (60) microseconds or less. In an additional embodiment, the programmable pulse duration has a range from thirty (30) microseconds to four hundred fifty 450 microseconds. In a further embodiment, the programmable pulse duration has a range from sixty (60) microseconds to four hundred fifty 450 microseconds. The programmable pulse duration can also have a range from thirty (30) microseconds to ten (10) milliseconds. Other combinations of pulse duration ranges are also possible.

The electrical pulses can also have a programmable waveform. For example, the electrical pulses can be a train of square or rectangular waves with a negative polarity. Additional examples include, but are not limited to, ramping pulse shapes, and pulse trains. In addition, so-called conditioning pulse sequences used before, during, or after therapy pulses may also be used. Other wave shapes and polarities are also possible.

In addition, the electrical pulses can have a programmable frequency. For example, the programmable frequency can be at least 10 Hz. Alternatively, the programmable frequency can be at least 100 Hz. The programmable frequency can also be at least 250 Hz. Alternatively, the programmable frequency can be 1000 Hz or less. The programmable frequency can also be 250 Hz or less. Alternatively, the programmable frequency can be 100 Hz or less. The programmable frequency can have a range of 10 Hz to 1000 Hz. Alternatively, the programmable frequency has a range of 100 Hz to 250 Hz. Other combinations of programmable frequency ranges are also possible.

The electrical pulses also have a programmable amplitude. For example, the programmable amplitude of each electrical pulse can be at least 0.1 volts. Alternatively, the programmable amplitude of each electrical pulse can be at least 0.5 volts. The programmable amplitude of each electrical pulse can also be at least 20 volts. The programmable amplitude of each electrical pulse can also be 100 volts or less. The programmable amplitude can also have a range of 0.1 volts to 100 volts. Alternatively, the programmable amplitude has a range of 0.5 volts to 20 volts. These voltage values for the electrical pulses correspond approximately with a current for each electrical pulse of 1 milliAmperes to 10 milliAmperes.

In addition to providing the electrical pulses to the first and second brain locations, the present method also counts down a monitoring interval at 114. The monitoring interval is a programmable time value between measuring the level of electrical parameters of the battery. Preferably, the monitoring interval is at least once every three months. More preferably, the monitoring interval is at least once every thirty (30) days, where each day is twenty-four (24) hours. The measuring of the battery parameters may be also be at least once every seven (7) days, where each day is twenty-four (24) hours.

In one embodiment, the monitoring interval can change from measuring the battery parameter at least once every thirty (30) days to measuring the battery parameter at least once every seven (7) days when the battery nears its end of life. The indication of the battery nearing its end of life can be a pre-set interval from the time of implant. Alternatively, the indication of the battery nearing its end of life can be an interval programmed by the physician based on the knowledge of the operating conditions and the existing battery parameters.

When the monitoring interval has expired, the system, at 120, measures a level of at least one electrical energy parameter of the battery. Any number of electrical energy parameters can be used in measuring the battery. For example, the level of the electrical energy parameters can include a value of a voltage level of the battery. Alternatively, the level of the electrical energy parameters can include the value of a battery current drain of the battery. In addition, one or more levels of the electrical energy parameters can also be measured according to the present invention. For example, both the voltage and battery current capacity can be measured. During the measuring process at 120, electrical energy stimulation preferably continues to be provided to the first and second brain locations as it was in 110.

In addition to measuring the value of the electrical energy parameters, a percentage of a total voltage or a total current capacity of the battery can also be measures. For example, the value of the electrical energy parameter measured from the battery can be used along with an initial value of the electrical energy parameter, to determine a percentage value for the measured electrical energy parameter. So, in determining the percentage value for the voltage of the battery, the value of the currently measured voltage value is divided by the starting voltage value of the battery. Alternatively, the percentage value for the current of the battery, the value of the currently measured battery current capacity is divided by the starting battery current capacity. This calculated value could then be used as the percentage value in the current invention. The use of the percentage value for the measured electrical energy parameter will be more fully described below.

At 130, the level of the electrical energy parameter is compared to a preselected threshold. For example, when a voltage value of the battery is used as the level of the electrical energy parameter, a preselected threshold value for the voltage is programmed into the implantable system. Alternatively, when a battery current capacity is used as the level of the electrical energy parameter, a preselected threshold value for the current is programmed into the implantable system. Furthermore, a rate and/or an acceleration of battery depletion can also be used as a preselected threshold. In one embodiment, the preselected threshold, or thresholds, are programmable at the time of implant, and can be changed at any time under the direction of the physician or attending medical technician using a medical device programmer.

In one embodiment, determining the preselected threshold value to be used is based on an understanding of a rate at which the electrical energy parameter changes (e.g., the rate of voltage and/or current decrease in the battery). This rate will be dependent upon the frequency of the electrical pulses, along with the amplitude and duration of the pulses used with each individual patient.

In addition to the rate at which the battery is being depleted, the preselected threshold value can also be determined based on the requirements of the electrical pulses delivered after the preselected threshold has been meet. For example, in selecting the preselected threshold value the amount of electrical energy necessary to ensure that therapeutically effective electrical pulses can continue to be delivered until the battery is replaced needs to be taken into consideration. This value will depend on factors such as the amount of time it is likely to take the patient to realize that their implantable system needs attention and present themselves to their doctor.

An additional factor will include the time likely required for the hospital to plan and execute the replacement of the pulse generator of the implantable system. This time, along with the knowledge of the therapy delivered after a threshold has been reached, can help in determining a safe threshold value for the patient. Therefore, the preselected threshold value used will be highly dependent upon the patient's requirements and their accessibility to their physician.

Once the level of the electrical energy parameter has been compared to the preselected threshold, the system proceeds to 134. At 134, a determination is made as to whether the level of the electrical energy parameter has, or has not, exceeded the preselected threshold. When the electrical energy parameter fails to exceed the preselected threshold, the system continues to provide electrical energy to the first and second brain locations. In addition, the system also starts a new monitoring interval. Alternatively, when the electrical energy parameter exceeds the preselected threshold, the system proceeds to 140.

At 140, the electrical pulses to the first brain location are adjusted when the level of the electrical energy parameter reaches the preselected threshold. Adjusting the level of the electrical energy parameter can include, but is not limited to, withholding the electrical pulses from the first brain location. In other words, the electrical energy pulses continue to be delivered to the second brain location, but are withheld at the first brain location.

In one embodiment, the electrical energy pulses that continue to be delivered to the second brain location have the same parameter values as the electrical energy pulses delivered before the level of the electrical energy parameter reaches the preselected threshold. In other words, the electrical energy pulses to the second brain location are not adjusted after the electrical energy parameter of the battery reaches the preselected threshold.

In an additional embodiment, the electrical energy pulses that continue to be delivered to the second brain location can also be adjusted. For example, adjusting the electrical energy pulses delivered to the second brain location can include cyclically adjusting the electrical pulses to the second brain location. In one embodiment, cycling the electrical energy pulses delivered to the second brain location involves providing a first time interval of delivering electrical pulses at the second brain location followed by and a second time interval of withholding the electrical pulses to the second brain location. Both the first and second time intervals can be programmable values in the range of one hour or less. Alternatively, both the first and second time intervals can be programmable values in the range of one hour or more. In addition, the length of time for the first and second time intervals can be programmed with the same or different values. Preferably, the values for both the first and second time intervals are determined under the care and analysis of the patient's physician.

Adjusting the electrical energy pulses delivered to the second brain location can also include changing a value of one or more parameters of the electrical pulses delivered to the second brain location. For example, changing the value of the electrical energy pulses delivered to the second brain location can include changing a voltage level of electrical pulses. Alternatively, changing the value of the electrical energy pulses delivered to the second brain location can include changing a current level of electrical pulses. In addition, it is possible that both the battery current capacity and the voltage value of the electrical pulses delivered to the second brain location can also be changed.

Alternatively, adjusting the level of the electrical energy parameter includes adjusting the electrical pulses to both the first and second brain locations when the level of the electrical energy parameter reaches the preselected threshold. For example, each electrical pulse of the electrical pulses can be cycled between the first brain location and the second brain location. In one embodiment, the cycling of the electrical pulses between the first and second brain locations can be accomplished by delivering the electrical pulses in a one-to-one sequential ratio. Other ratios of pulses to the first and second brain locations are also possible, such as a two-to-one sequential ratio, a two-to-two sequential ratio, etc. In the present examples, the electrical energy pulses cycled between the first and second brain locations have the same parameter values (i.e., not adjusted) as the electrical energy pulses delivered before the level of the electrical energy parameter reaches the preselected threshold.

In an additional embodiment, the electrical energy pulses of the first and second brain locations can have adjusted parameter values as compared to the electrical energy pulses delivered before the level of the electrical energy parameter reaches the preselected threshold. For example, adjusting the electrical pulses can include changing a value of one or more parameters of the electrical pulses to the first brain location and the second brain location. In one embodiment, changing the value of one or more parameters includes changing a voltage level of electrical pulses. Alternatively, changing the value of one or more parameters includes changing a current level of electrical pulses. In an additional embodiment, changing the value of one or more parameters includes changing either the current level and/or the voltage level of electrical pulses that are delivered to either the first and/or second brain location.

It is understood that the above descriptions are illustrative, and that any adjustment that deceases power consumption in contemplated.

Figure 2:
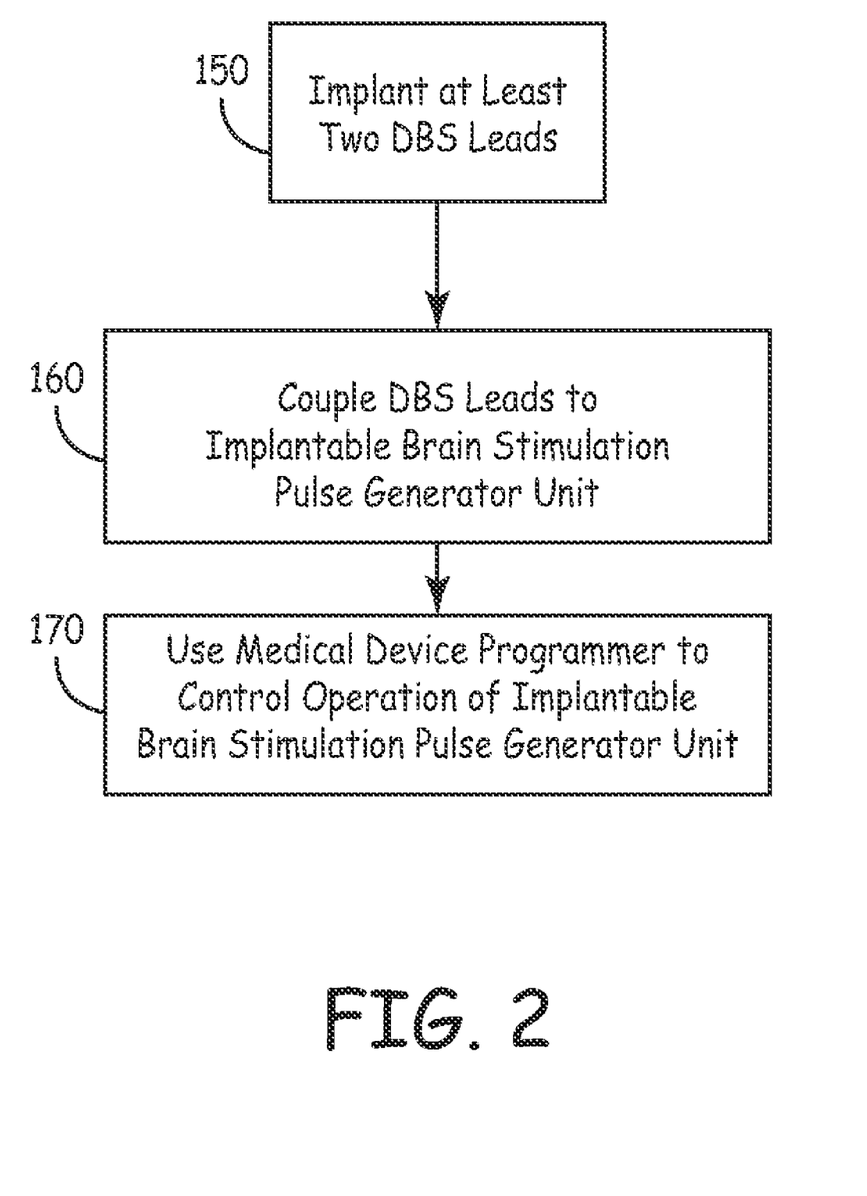
FIG. 2 is a flow chart illustrating a technique for implanting and programming an implantable brain electrical stimulation system according to one embodiment of the present invention.

FIG. 2 is a flow diagram illustrating a method of programming the brain electrical stimulation system of the present invention. At 150, at least two DBS leads are implanted into the brain of the patient. As previously discussed, the brain stimulation leads can be implanted into bilateral segments of the subthalamic nucleus or the globus pallidus. In one embodiment, the electrodes on the brain stimulation leads are implanted in such a way that the electrodes on the brain stimulation leads span the total linear cross section of the brain structure in which they are being implanted. In one example, the leads can be implanted through the use of neuroimaging, microelectrode recording, stimulation, and/or stereotactic techniques into their respective positions within the brain of the patient.

At 160, the DBS leads of the present invention are operatively coupled to an implantable brain stimulation pulse generator unit. The pulse generator unit has control circuitry, as described below, that is capable of storing and executing executable programs and accessing stored data and instruction sets that are used in providing therapy to the patient. The pulse generator unit also has the ability to communicate with and be programmed through the medical device programmer, as described below. This is typically done through a telemetric link established between the pulse generator unit and the medical device programmer. These aspects of the present invention will be discussed more fully below.

Once the pulse generator unit has been coupled to the DBS leads, the medical device programmer can be used at 170 to control the operation of the pulse generator unit. Operation instructions for the pulse generator unit can be entered via the medical device programmer. The pulse generator unit can then execute these instructions. The physician can provide operation instructions to the pulse generator unit in an effort to find the most appropriate treatment regimen for the patient's condition. Often times this is an iterative process between the patient and the physician, as the patient is typically conscious during these types of procedures. Based on the feedback of the patient, the proper location of the DBS leads can be determined by the physician. In addition to the location, the electrical energy parameters of the electrical energy pulses to the first and second brain locations can also be adjusted and programmed into the pulse generator unit.

In addition to determining and programming the parameter values of the electrical energy pulses used in the first and second brain locations, the physician and the patient can also identify which adjustments will be made to the parameters of the electrical energy pulses if the system were to determine that one or more electrical energy parameters had reached a preselected threshold. So, for example, the physician can test the patient's response when the electrical pulses to the first brain location are adjusted in the ways previously described. In addition, the physician could also test the patient's response when the electrical pulses to first and/or second brain location are adjusted in the ways previously described.

As will be appreciated, adjusting the electrical pulses to first and/or second brain location as described herein results in less battery energy being used as compared to before the adjustment. Because less battery energy is being used after the adjustment, the useful life of the battery is extended. In addition to the extended battery life, the adjustment also allows some physical symptoms alleviated by the implantable system to return, thereby signaling the patient that medical attention needs to be sought. During the implant procedure, the physician and patient can attempt to isolate and identify which physical symptoms will return if the implantable system adjusts the electrical pulses to first and/or second brain locations. As previously discussed, these returning symptoms are such that the patient is not placed in an undesirable state.

In one embodiment, the preselected threshold for the electrical energy parameter can be set to a few tenths of a volt below the starting voltage value of the battery. For example, when the starting voltage value of the battery is 3.7 volts, the preselected threshold could be 3.5 volts. The exact voltage value used for the preselected threshold can depend upon the electrochemistry of the battery being used. Alternatively, the preselected threshold for the electrical energy parameter can be set to about ninety (90) percent of the total energy that a new battery can deliver. For example, a typical battery for a bilateral stimulator system can have a total capacity of about 6 AmpHour. A typical threshold for the current used could be set at about 0.5 AmpHour, where about ninety (90) percent of the total energy (5.5 AmpHour) of the battery has been delivered.

In addition to programming specific values for the preselected threshold (e.g., a set voltage value and/or a set current value), it is also possible to have the preselected threshold be in the form of a preselected percentage. The preselected percentage value is programmed into the implantable system and is compared to a percentage value determined for the level of electrical energy parameter. For example, the percentage value is determined from the level of the electrical energy parameter measured in the battery and an initial value of the electrical energy parameter. The percentage value is then compared to the preselected percentage value. In one embodiment, the preselected percentage is a programmable value set as five (5) percent or less of the initial value of the electrical energy parameter. In an additional embodiment, the preselected percentage is a programmable value set as ten (10) percent or less of the initial value of the electrical energy parameter.

When the percentage of the electrical energy parameter reaches the preselected percentage of the initial value of the electrical energy parameter, the value of one or more of the electrical energy parameters of the stimulation therapy is then adjusted. In one embodiment, adjusting the electrical energy parameters of the stimulation therapy includes changing the values of the electrical energy parameters to the first brain location and/or the second brain location as previously described.

In one embodiment, the initial value of the electrical energy parameter is determined and programmed at the time the system is implanted into the patient. Alternatively, the initial value of the electrical energy parameter is a set value that cannot be changed or programmed. Examples of the initial value of the electrical energy parameter include the initial voltage and/or current rating of the battery used in the implantable system.

In an additional embodiment, the patient can use the medical device programmer to interrogate the implantable brain stimulation pulse generator unit to determine one or more electrical energy parameter values for the battery. Based on this information, the patient can then use the medical device programmer to make one or more adjustments in the electrical energy stimulation pulses, as described.

Figure 3:
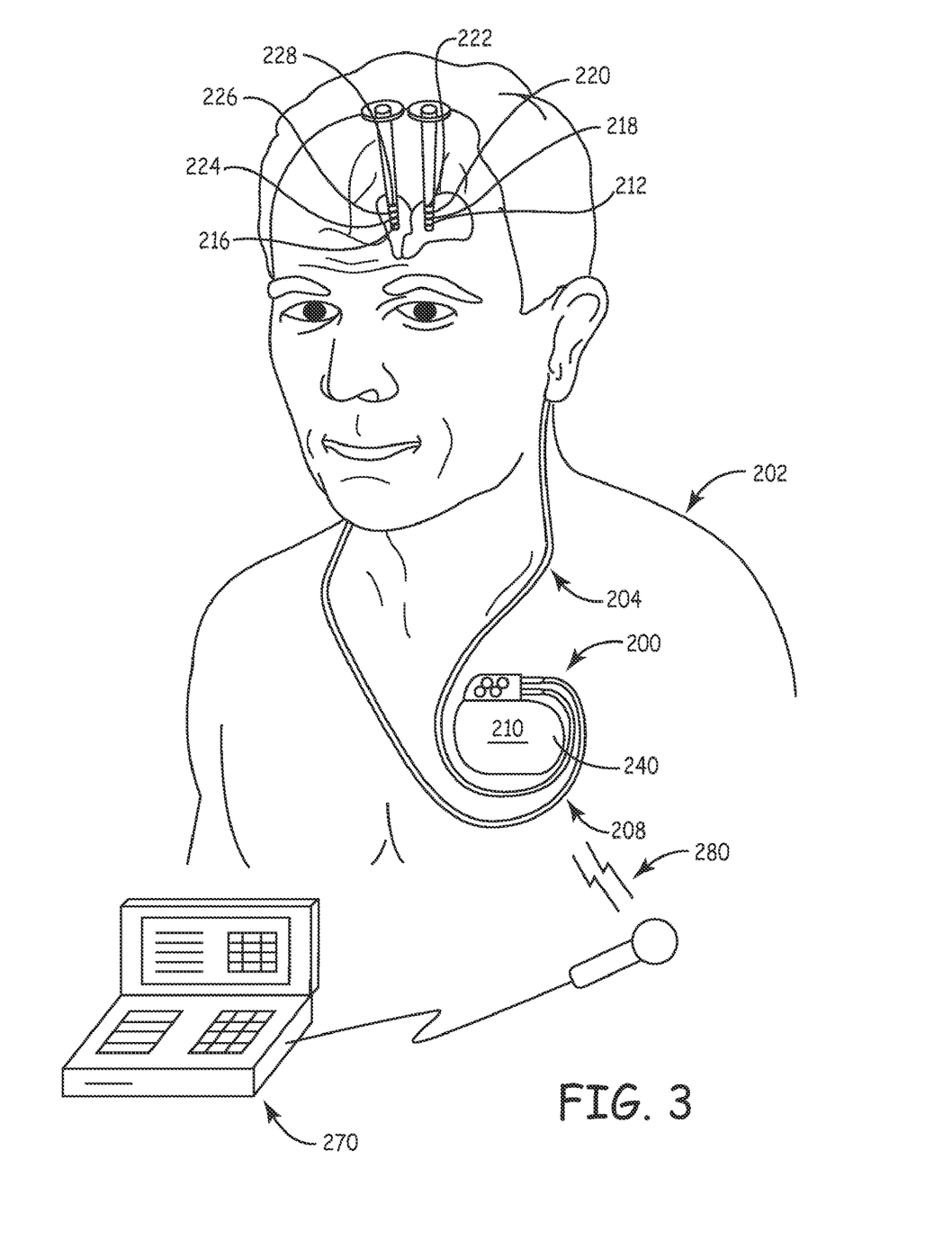
FIG. 3 is a schematic diagram illustrating an implantable medical device system according to one embodiment of the present invention.

FIG. 3 is a schematic illustration showing an example of a brain electrical stimulation system 200 implanted in a patient 202. The brain electrical stimulation system 200 includes at least a first brain stimulation lead 204, a second brain stimulation lead 208 and an implantable brain stimulation pulse generator unit 210. The first brain stimulation lead 204 includes an electrode 212 and the second brain stimulation lead 208 includes an electrode 216. Preferably, each of the first brain stimulation lead 204 and the second brain stimulation lead 208 include two or more electrodes.

In a preferred embodiment, the first brain stimulation lead 204 is a quadpole lead that includes the electrode 212, a second electrode 218, a third electrode 220, and a fourth electrode 222. Each of the electrodes 212, 218, 220 and 222 are spaced apart and are electrically isolated from each other. In addition, the second brain stimulation lead 208 is also a quadpole lead that includes the electrode 216, a second electrode 224, a third electrode 226, and a fourth electrode 228. Each of the electrodes 216, 224, 226 and 228 are also spaced apart and are electrically isolated from each other.

Electrodes 212, 218, 220, 222 on the first lead 204, and electrodes 216, 224, 226 and 228 on the second lead 208 are releasably and operatively coupled to the implantable brain stimulation pulse generator unit 210. Electrodes 212, 218, 220, 222 on the first lead 204, and electrodes 216, 224, 226 and 228 on the second lead 208 can be used to sense one or more electrical field potentials from the brain with the implantable brain stimulation pulse generator unit 210. In addition, the implantable brain stimulation pulse generator unit 210 can be used to provide electrical pulses through the electrodes 212, 218, 220, 222 on the first lead 204, and electrodes 216, 224, 226 and 228 on the second lead 208. In one example, unipolar pulses can be delivered between one of electrodes 212, 218, 220, 222 on the first lead 204, and one electrodes 216, 224, 226 and 228 on the second lead 208 and the housing 240 of the generator unit 210. Alternatively, monopolar and/or bipolar pulses can be delivered between any combination of two or more electrodes 212, 218, 220, 222 on the first lead 204, and any combination of two or more electrodes 216, 224, 226 and 228 on the second lead 208.

The implantable brain stimulation pulse generator unit 210 further includes a stimulation unit, a power monitor, and an electrical power supply (all discussed more fully below), all of which are preferably hermetically sealed in an implantable housing 240. At least a portion of the implantable housing 240 may be conductive to allow the housing 240 to be used as a pole in sensing and delivering electrical energy pulses to the brain. The stimulation unit is coupled to the electrical power supply and to the power monitor. The stimulation unit operates to provide electrical pulses to the electrodes 212, 218, 220 and 222 on the first lead 204, and to electrodes 216, 224, 226, 228 on the second lead 208.

The implantable brain stimulation pulse generator unit 210 further includes a controller in the form of, e.g., a microprocessor and memory (discussed more fully below), both of which are operatively coupled to the electrical power supply, the stimulation unit and the power monitor. The controller is one form of operatively coupling the stimulation unit and the power monitor.

In one embodiment, the microprocessor is used to execute executable programs stored in memory. These programs can include those for controlling the power monitor to measure the level of the electrical energy parameter in the electrical power supply, compare the level of the electrical energy parameter to the preselected threshold, and to cause the stimulation unit to adjust the electrical pulses to the first brain location when the level of the electrical energy parameter reaches the preselected threshold, as previously described.

In addition, the system 200 may also include a telemetry receiver/transmitter for receiving and transmitting electronic data and/or electronic instructions between the implantable brain stimulation pulse generator unit 210 and an optional medical device programmer/controller 270. In one example, communication between the implantable brain stimulation pulse generator unit 210 and the medical device programmer/controller 270 occurs through a telemetric data link 280 established between the two devices.

Examples of the first brain stimulation lead 204 and the second brain stimulation lead 208 having two or more electrodes can include, but are not limited to, lead model 3387 DBS™ sold by Medtronic, Inc. of Minneapolis, Minn., lead model 3388 DBS™, and/or lead model 3389 DBS™, also sold by Medtronic, Inc. Other DBS leads having two or more electrodes may also be useful with the present invention.

Figure 4:
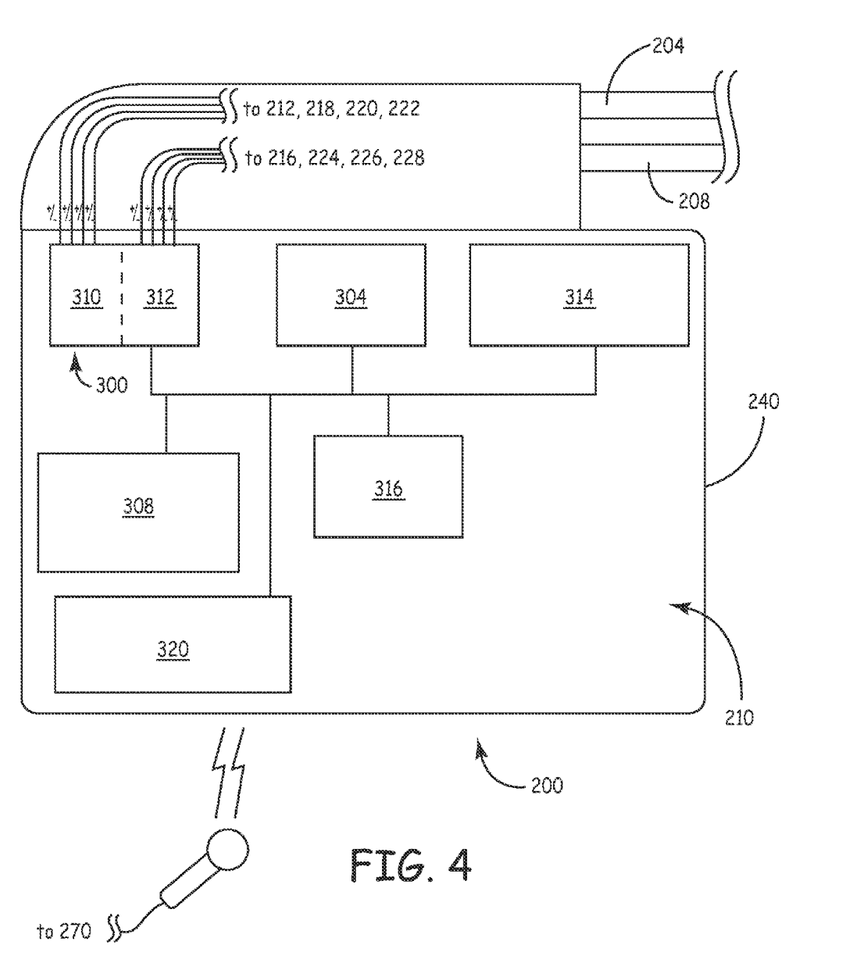
FIG. 4 is a block diagram of an implantable medical device system according to one embodiment of the present invention.

FIG. 4 is a block diagram showing an example of the brain electrical stimulation system 200. The brain electrical stimulation system 200 includes at least the first brain stimulation lead 204, the second brain stimulation lead 208 and the implantable brain stimulation pulse generator unit 210, as described above. The implantable brain stimulation pulse generator unit 210 further includes a stimulation unit 300, a power monitor 304, and an electrical power supply 308, all of which are preferably hermetically sealed in an implantable housing 240. The stimulation unit 300 is coupled to the electrical power supply 308 and to the power monitor 304.

The stimulation unit 300 also includes a first channel 310 and a second channel 312. The first channel 310 can provide electrical pulses through one or more of the electrodes 212, 218, 220 and/or 222 on the first lead 204, as previously discussed. Similarly, the second channel 312 can provide electrical pulses through one or more of the electrodes 216, 224, 226 and/or 228 on the second lead 208, as previously discussed. At least a portion of the implantable housing 240 may also be conductive to allow the housing 240 to be used as a pole in sensing and delivering electrical energy pulses to the brain.

The implantable brain stimulation pulse generator unit 210 further includes a controller in the form of, e.g., a microprocessor 314 and memory 316, both of which are operatively coupled to the electrical power supply 308, the stimulation unit 300 and the power monitor 304. The controller is one form of operatively coupling the stimulation unit 300 and the power monitor 304. In one embodiment, the electrical power supply 308 can take the form of a battery. As previously discussed, the battery can include one or more electrochemical cells adapted for use in a hermetically sealed implantable medical device.

In one embodiment, the microprocessor 314 is used to execute executable programs stored in memory 316. These programs can include those for controlling the power monitor 304 to measure the level of the electrical energy parameter in the electrical power supply 308 and to compare the level of the electrical energy parameter to the preselected threshold, and to cause the stimulation unit 300 to adjust the electrical pulses from the first channel 310 to the first brain location when the level of the electrical energy parameter reaches the preselected threshold, as previously described. In addition, the microprocessor 314 includes a clock function for providing timing functions to allow for the time intervals used in the present invention to be counted.

In one example, the microprocessor 314 can be used to count the monitoring interval. At the expiration of the monitoring interval, the microprocessor 314 instructs the power monitor 304 to analyze and measure the level of the electrical energy parameter, or parameters, in the electrical power supply 308. As previously discussed, the time interval levels used in the implantable brain stimulation pulse generator unit 210 can be programmable values entered through the use of the medical device programmer/controller 270. The monitoring interval can include any number of time values, including those previously discussed.

At the expiration of the monitoring interval, the power monitor 304 can then be used to analyze and measure the level of the electrical energy parameter in the electrical energy power supply 308. In one example, the power monitor 304 can measure the voltage and/or the current of the electrical power supply 308 as the electrical energy parameter. The power monitor 304 can then be used to compare the measured electrical energy parameter to the value of the preselected threshold. As discussed, values for the preselected thresholds can be stored and accessed in the memory 316. Preselected threshold values for the electrical energy parameter can include those previously discussed. The power monitor 304 can then cause the stimulation unit 300 to adjust the electrical pulses from the first channel 310 to one or more of the electrodes 212, 218, 220 and/or 222 on the first brain stimulation lead 204 when the level of the electrical energy parameter reaches the preselected threshold.

In an alternative embodiment, the power monitor 304 can calculate a percentage of an initial value for the electrical energy parameter of the electrical power supply 308. For example, a preselected percentage of the initial value of the electrical energy parameter can be used as the preselected threshold. In one embodiment, the preselected threshold can be five (5) percent or less of the initial value of the electrical energy parameter. Alternatively, the preselected threshold can be ten (10) percent or less of the initial value of the electrical energy parameter. When measuring the level of the electrical energy parameter, the power monitor 304 determines a present value for an electrical energy parameter (e.g., the present value for the current and/or the voltage). The power monitor 304 then uses an initial value for the electrical energy parameter, or parameters, that was measured and stored when the electrical power supply 308 was put into service, in determining the percentage of the initial value of the electrical energy parameter. The power monitor 304 can then cause the stimulation unit 300 to adjust the electrical pulses from one or both of the first and/or second channels 310, 312 when the level of the electrical energy parameter reaches the preselected percentage of the initial value of the electrical energy parameter.

In one embodiment, the power monitor 304 can be used to adjust the stimulation unit 300 to withhold electrical pulses from the first channel to one or more of the electrodes 212, 218, 220, and/or 222 on the first lead 204 when the level of the electrical energy parameter reaches the preselected threshold. In one example, values for the preselected threshold are stored in the memory 316 and accessible to the executable programs used with and by the power monitor 304. The power monitor 304 can also cyclically adjust the electrical pulses from the second channel 312 to one or more of the electrodes 216, 224, 226, 228 on the second lead 208 after the level of the electrical energy parameter reaches the preselected threshold. For example, the power monitor 304 can cyclically adjust the electrical pulses between the first interval of providing the electrical pulses and the second interval of withholding the electrical pulses, as described above. Programmable values for the first interval and the second interval can be stored and accessed in memory 316.

Alternatively, the power monitor 304 can adjust one or more parameters of the electrical pulses from the second channel 312 to one or more of the electrodes 216, 224, 226, 228 on the second lead 208 when the level of the electrical energy parameter reaches the preselected threshold, as previously described. For example, the power monitor 304 can adjust the voltage level of electrical pulses and/or the current level of the electrical pulses, as previously described. The power monitor 304 can also cause the stimulation unit 300 to adjust electrical pulses from the second channel 312 to one or more of the electrodes 216, 224, 226, 228 on the second lead 208, in addition to adjusting the electrical pulses from the first channel 310 to one or more of the electrodes 212, 218, 220, 222 on the first lead 204. For example, the power monitor 304 can adjust the electrical pulses by cycling each electrical pulse of the electrical pulses between one or more of the electrodes 212, 218, 220, 222 on the first lead 204 and one or more of the electrodes 216, 224, 226, 228 on the second lead 208 at the preselected interval. As previously described, this can be done when the level of the electrical energy parameter being measured by the power monitor 304 reaches the preselected threshold.

In addition, the power monitor 304 can also adjust one or more parameters of the electrical pulses from the first and second channels 310 and 312 to one or more of the electrodes 212, 218, 220, 222 on the first lead 204 and one or more of the electrodes 216, 224, 226, 228 on the second lead 208, respectively, when the level of the electrical energy parameter reaches the preselected threshold. In this situation, the power monitor 304 can adjust, for example, the voltage level of electrical pulses delivered by the first channel 310 and the second channel 312 of stimulation unit 300 to the one or more of the electrodes 212, 218, 220, 222 on the first lead 204 and the one or more of the electrodes 216, 224, 226, 228 on the second lead 208, respectively, when the level of the electrical energy parameter reaches the preselected threshold. Alternatively, the power monitor 304 can adjust, for example, the current level of electrical pulses delivered by the channels 310 and 312 of the stimulation unit 300 to the one or more of the electrodes 212, 218, 220, 222 on the first lead 204 and the one or more of the electrodes 216, 224, 226, 228 on the second lead 208, respectively, when the level of the electrical energy parameter reaches the preselected threshold. The power monitor 304 can also be programmed to adjust any combination of current level changes and voltage level change for one or more of the electrodes on the first lead 204 and/or the second lead 208.

In addition, the implantable brain stimulation pulse generator unit 210 may also include a telemetry receiver/transmitter 320 for receiving and transmitting electronic data and/or electronic instructions between the microprocessor 310, the power monitor 304 and the memory 314 and the medical device programmer/controller 270.

The preceding specific embodiments are illustrative for the practice of the invention. It is to be understood, therefore, that other expedients known to those skilled in the art or disclosed herein, may be employed without departing from the invention or the scope of the appended claims. For example, the present invention is not limited to a bilateral lead system as described above. It is recognized that the present invention could be used with a system having more than two leads for brain stimulation, wherein electrical energy pulses to one or more of the leads and/or electrodes on the leads are adjusted to not only extend the life of the battery, but also serves to allow some physical symptoms alleviated by the system to return, thereby signaling the patient that medical attention needs to be sought. The present invention further includes within its scope methods of making and using systems and/or apparatus for carrying out the methods described hereinabove.

What is claimed is:

1. An electrical stimulation system comprising:
 a first stimulation lead comprising an electrode;
 a second stimulation lead comprising an electrode; and
 an implantable stimulation pulse generator unit, wherein
  the electrode on the first stimulation lead and the
  electrode on the second stimulation lead are operatively coupled to the implantable pulse generator unit, the implantable pulse generator unit comprising;

an electrical power supply;

a stimulation unit coupled to the electrical power supply, wherein the stimulation unit is operable to provide electrical pulses to the electrode on the first stimulation lead and the electrode on the second stimulation lead; and a power monitor operatively coupled to the stimulation unit, wherein the power monitor is operable to measure a level of an electrical energy parameter for the electrical power supply and is operable to cause the stimulation unit to cycle the electrical pulses generated by the stimulation unit between the electrode on the first stimulation lead and the electrode on the stimulation lead when the level of the electrical energy parameter reaches a preselected threshold.

2. The electrical stimulation system of claim 1, wherein the power monitor is operable to adjust one or more parameters of the electrical pulses to the electrode on the second stimulation lead when the level of the electrical energy parameter reaches the preselected threshold.

3. The electrical stimulation system of claim 2, wherein the power monitor is operable to adjust a voltage level of electrical pulses.

4. The electrical stimulation system of claim 2, wherein the power monitor is operable to adjust a current level of electrical pulses.

5. The electrical stimulation system of claim 1, wherein the power monitor measures a voltage of the electrical power supply as the electrical energy parameter.

6. The electrical stimulation system of claim 1, wherein the power monitor measures a current of the electrical power supply as the electrical energy parameter.

7. The electrical stimulation system of claim 1, wherein the preselected threshold comprises a preselected percentage of an initial value of the electrical energy parameter, and the power monitor is operable to cause the stimulation unit to adjust electrical pulses when the level of the electrical energy parameter reaches the preselected percentage of the initial value of the electrical energy parameter.

8. The electrical stimulation system of claim 7, wherein the power monitor is operable to measure voltage as the electrical energy parameter, and the preselected percentage is ten (10) percent or less of the initial value of the electrical energy parameter.

9. The electrical stimulation system of claim 7, wherein the power monitor is operable to measure current as the electrical energy parameter, and the preselected percentage is ten (10) percent or less of the initial value of the electrical energy parameter.

10. The electrical stimulation system of claim 1, wherein the stimulation unit is operable to provide electrical pulses having a pulse duration of at least 30 microseconds.

11. The electrical stimulation system of claim 1, wherein the stimulation unit is operable to provide electrical pulses having a frequency of at least 10 Hz.

12. The electrical stimulation system of claim 11, wherein the stimulation unit is operable to provide electrical pulses having a negative square wave profile and an amplitude of at least 0.1 volts.

13. The electrical stimulation system of claim 1, wherein the first stimulation lead and the second stimulation lead each comprise two or more electrodes, where the two or more electrodes are electrically separated and spaced apart along the first stimulation lead and the second stimulation lead.

14. The electrical stimulation system of claim 1, wherein the power monitor measures the level of the electrical energy parameter for the electrical power supply at least once every thirty (30) days.

15. An implantable stimulation pulse generator unit comprising:

an electrical power supply;

a stimulation unit coupled to the electrical power supply, wherein the stimulation unit comprises a first channel and a second channel operable for providing electrical pulses through the first channel and the second channel; and a power monitor coupled to the stimulation unit, wherein the power monitor is operable to measure a level of an electrical energy parameter for the electrical power supply and is operable to cause the stimulation unit to cycle the electrical pulses generated by the stimulation unit between the first channel and the second channel when the level of the electrical energy parameter reaches a preselected threshold.

16. The implantable stimulation pulse generator unit of claim 15, wherein the power monitor is operable to adjust one or more parameters of the electrical pulses from the second channel when the level of the electrical energy parameter reaches the preselected threshold.

17. The implantable stimulation pulse generator unit of claim 16, wherein the power monitor is operable to adjust a voltage level of electrical pulses.

18. The implantable stimulation pulse generator unit of claim 16, wherein the power monitor is operable to adjust a current level of electrical pulses.

19. The implantable stimulation pulse generator unit of claim 15, wherein the power monitor is operable to measure a voltage of the electrical power supply as the electrical energy parameter.

20. The implantable stimulation pulse generator unit of claim 15, wherein the power monitor is operable to measure a current of the electrical power supply as the electrical energy parameter.

21. The implantable stimulation pulse generator unit of claim 15, wherein the preselected threshold comprises a preselected percentage of an initial value of the electrical energy parameter, and the power monitor is operable to cause the stimulation unit to adjust electrical pulses when the level of the electrical energy parameter reaches the preselected percentage of the initial value of the electrical energy parameter.

22. The implantable stimulation pulse generator unit of claim 21, wherein the power monitor is operable to measure voltage as the electrical energy parameter, and the preselected percentage is ten (10) percent or less of the initial value of the electrical energy parameter.

23. The implantable stimulation pulse generator unit of claim 21, wherein the power monitor is operable to measure current as the electrical energy parameter, and the preselected percentage is ten (10) percent or less of the initial value of the electrical energy parameter.

24. The implantable stimulation pulse generator unit of claim 15, wherein the stimulation unit is operable to provide electrical pulses having a pulse duration of at least 30 microseconds.

25. The implantable stimulation pulse generator unit of claim 15, wherein the stimulation unit is operable to provide electrical pulses having a frequency of at least 10 Hz.

26. The implantable stimulation pulse generator unit of claim 25, wherein the stimulation unit is operable to provide electrical pulses having a negative square wave profile and an amplitude of at least 0.1 volts.

27. The implantable stimulation pulse generator unit of claim 22, wherein the first channel is adapted to be releasably coupled to two or more electrodes, and the second channel is adapted to be releasably coupled to two or more electrodes.

28. The implantable stimulation pulse generator unit of claim 15, wherein the power monitor is operable to measure the level of the electrical energy parameter for the electrical power supply at least once every thirty (30) days.

29. A method of stimulation comprising:
   providing electrical pulses to a first brain location and a second brain location using a battery;
   measuring a level of an electrical energy parameter of the battery;
   comparing the level of the electrical energy parameter to a preselected threshold; and
   cycling the electrical pulses between the first brain location and the second brain location when the level of the electrical energy parameter reaches the preselected threshold.

30. The method of stimulation of claim 29, wherein the preselected threshold comprises a preselected percentage of an initial value of the electrical energy parameter, and wherein comparing the level of the electrical energy parameter to the preselected threshold comprises determining a percentage of the electrical energy parameter from the level of the electrical energy parameter measured and the initial value of the electrical energy parameter, and wherein cycling the electrical pulses is initiated when the percentage of the electrical energy parameter reaches the preselected percentage of the initial value of the electrical energy parameter.

31. The method of brain stimulation of claim 30, comprising setting the preselected percentage as ten (10) percent or less of the initial value of the electrical energy parameter.

32. The method of stimulation of claim 29, wherein providing electrical pulses comprises providing electrical pulses to a first half of a brain structure for the first location and providing electrical pulses to a second half of the brain structure for the second location.

33. A brain electrical stimulation system comprising:
   a first brain stimulation lead comprising an electrode;
   a second brain stimulation lead comprising an electrode; and
   an implantable brain stimulation pulse generator unit, wherein the electrode on the first brain stimulation lead and the electrode on the second brain stimulation lead are operatively coupled to the implantable pulse generator unit, the implantable pulse generator unit comprising:
      an electrical power supply;
      a stimulation unit coupled to the electrical power supply, wherein the stimulation unit is operable to provide electrical pulses to the electrode on the first brain stimulation lead and the electrode on the second brain stimulation lead; and
   a power monitor operatively coupled to the stimulation unit, wherein the power monitor is operable to measure a level of an electrical energy parameter for the electrical power supply and is operable to cause the stimulation unit to withhold electrical pulses to the electrode on the first brain stimulation lead and adjust the electrical pulses to the electrode on the second brain stimulation lead when the level of the electrical energy parameter reaches a preselected threshold.

* * * * *

UNITED STATES PATENT AND TRADEMARK OFFICE
CERTIFICATE OF CORRECTION

PATENT NO. : 7,295,880 B2  Page 1 of 1
APPLICATION NO. : 10/133466
DATED : November 13, 2007
INVENTOR(S) : Frans L. H. Gielen It is certified that error appears in the above-identified patent and that said Letters Patent is hereby corrected as shown below:

Col. 17, Line 15: "the stimulation" should read --the second stimulation--

Col. 19, Line 2: "claim 22" should read --claim 15--

Col. 19, Line 10: "of stimulation" should read --of brain stimulation--

Col. 19, Line 20: "of stimulation" should read --of brain stimulation--

Col. 20, Line 1: "of stimulation" should read --of brain stimulation--

Signed and Sealed this

Twenty-fifth Day of November, 2008

JON W. DUDAS
*Director of the United States Patent and Trademark Office*